US012062449B2

(12) United States Patent
Hussain et al.

(10) Patent No.: US 12,062,449 B2
(45) Date of Patent: Aug. 13, 2024

(54) MACHINE LEARNING TECHNIQUES FOR PREDICTIVE CLINICAL INTERVENTION RECOMMENDATION

(71) Applicant: UnitedHealth Group Incorporated, Minnetonka, MN (US)

(72) Inventors: Reem A. Hussain, Silver Spring, MD (US); Vijay S. Nori, Roswell, GA (US); Daniel J. Mulcahy, Evanston, IL (US); Jason E. Weinberg, Galesburg, IL (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 262 days.

(21) Appl. No.: 17/538,521

(22) Filed: Nov. 30, 2021

(65) Prior Publication Data
US 2023/0170093 A1  Jun. 1, 2023

(51) Int. Cl.
*G16H 50/20* (2018.01)
*G06N 3/082* (2023.01)
(Continued)

(52) U.S. Cl.
CPC ............. *G16H 50/20* (2018.01); *G06N 3/082* (2013.01); *G16H 10/60* (2018.01); *G16H 20/00* (2018.01)

(58) Field of Classification Search
CPC ........ G16H 10/60; G16H 15/00; G16H 20/60; G16H 50/20; H04W 4/021; G06Q 10/1093; G06Q 10/0639
(Continued)

(56) References Cited

U.S. PATENT DOCUMENTS 8,407,081 B1 *  3/2013  Rajasenan .......... G06Q 10/0639
                                                705/7.42
10,614,919 B1    4/2020  Yedwab et al.
(Continued)

FOREIGN PATENT DOCUMENTS

CA     2878568 A1 *  4/2013  ......... A61B 5/02028
WO  2020/239574 A1   12/2020

OTHER PUBLICATIONS

Involvement of Machine Learning Tools in Healthcare Decision Making, Senerath Mudalige Don Alexis Chinthaka Jayatilake Gamage Upeksha Ganegoda, Hindawi Journal of Healthcare Engineering, Published Jan. 27, 2021 (Year: 2021).*
(Continued)

*Primary Examiner* — Dilek B Cobanoglu
(74) *Attorney, Agent, or Firm* — Alston & Bird LLP

(57) ABSTRACT

Various embodiments of the present invention utilize systems, methods, and computer program products that perform predictive data analysis operations by using an agent machine learning model to determine an optimal clinical intervention based at least in part on the current clinical state and an inferred reinforcement learning policy that is determined based at least in part on a familiarity-adjusted reward function, where the familiarity-adjusted reward function is generated by an environment machine learning framework based at least in part on one or more next state predictions for one or more pruned action-state combinations based at least in part on a historical clinical outcome database, and the one or more pruned action-state combinations are determined based at least in part on one or more pruned clinical actions that are selected from a plurality of candidate clinical actions based at least in part on one or more action pruning criteria.

20 Claims, 7 Drawing Sheets

(51) Int. Cl.
*G16H 10/60* (2018.01)
*G16H 20/00* (2018.01)

(58) Field of Classification Search
USPC .......................................... 705/2, 3, 4, 7.42
See application file for complete search history.

(56) References Cited

U.S. PATENT DOCUMENTS

| | | |
|---|---|---|
| 11,056,242 B1 * | 7/2021 | Jain .................. G16H 10/60 |
| 11,127,506 B1 * | 9/2021 | Jain .................. H04W 4/021 |
| 11,488,714 B2 * | 11/2022 | Shankar ............. G16H 20/60 |
| 2010/0174555 A1 | 7/2010 | Abraham-Fuchs et al. |
| 2019/0392924 A1 | 12/2019 | Bettencourt-Silva et al. |
| 2020/0111578 A1 | 4/2020 | Koblick et al. |
| 2020/0234826 A1 | 7/2020 | Said |
| 2020/0357526 A1 | 11/2020 | Odiz et al. |
| 2020/0373017 A1 | 11/2020 | Wang |
| 2021/0057098 A1 | 2/2021 | Mulligan et al. |
| 2021/0082573 A1 | 3/2021 | Pecora et al. |
| 2021/0166816 A1 * | 6/2021 | Khan ................ G06Q 10/1093 |
| 2021/0174962 A1 * | 6/2021 | Hill, Jr. .............. G16H 15/00 |
| 2023/0142594 A1 * | 5/2023 | Eberhardt, III ........ G16H 50/20 705/4 |

OTHER PUBLICATIONS

"CDS Authoring Tool | CDS Connect," Agency For Healthcare Research and Quality, (2 pages), (online), [Retrieved from the Internet Feb. 25, 2022] <URL: https://cds.ahrq.gov/cdsconnect/authoring>.

"Comorbidities Tool From BMJ Best Practice," (7 pages), (Year: 2021), (article, online), [Retrieved from the Internet Aug. 27, 2021] <URL: https://bestpractice.bmj.com/info/us/comorbidities/>.

"Guidelines," MDCalc, (10 pages), (online), [Retrieved from the Internet Feb. 25, 2022] <URL: https://www.mdcalc.com/guidelines>.

Abidi, Samina. "A Knowledge-Modeling Approach To Integrate Multiple Clinical Practice Guidelines To Provide Evidence-Based Clinical Decision Support For Managing Comorbid Conditions," Journal of Medical Systems, vol. 41, No. 193, Oct. 26, 2017, pp. 1-19.

Fdez-Olivares, Juan et al. "Personalized Conciliation Of Clinical Guidelines For Comorbid Patients Through Multi-Agent Planning," Artificial Intelligence In Medicine, vol. 96, Nov. 23, 2018, (35 pages), DOI: 10.1016/j.artmed.2018.11.003.

Kidambi, Rahul et al. "MOReL: Model-Based Offline Reinforcement Learning," arXiv preprint arXiv:2005.05951v1 [cs.LG] May 12, 2020, (25 pages), Available online: https://arxiv.org/pdf/2005.05951v1.pdf.

Nemati, Shamim et al. "Optimal Medication Dosing from Suboptimal Clinical Examples: A Deep Reinforcement Learning Approach," In 2016 38th Annual International Conference of the IEEE Engineering In Medicine and Biology Society (EMBC), Aug. 16, 2016, pp. 2978-2981, IEEE, Available online: https://drive.google.com/file/d/1Hyx_9zezOUrO4UykwkEKDyYkNR_kw84c/view.

Prasad, Niranjani et al. "A Reinforcement Learning Approach to Weaning of Mechanical Ventilation in Intensive Care Units," arXiv preprint arXiv:1704.06300v1 [cs.AI] Apr. 20, 2017, (10 pages), Available online: https://arxiv.org/pdf/1704.06300.pdf.

Silver, David et al. "Mastering The Game Of Go With Deep Neural Networks and Tree Search," Nature, vol. 529, No. 7587, Jan. 28, 2016, (20 pages).

* cited by examiner

| optimal_actions_list 601 | next_states_list 602 |
|---|---|
| ['antidiabetic_combination_agents' 'dipeptidyl_peptidase_inhibitors' 'metformin'] 611 | ['DM_1' 'RUB_0'] 621 |
| ['insulin' 'metformin' 'sodium-glucose_co-transporter_2_inhibitors' 'sulfonylurea'] 612 | ['DM_1' 'RUB_0'] 621 |
| ['metformin' 'sodium-glucose_co-transporter_2_inhibitors'] | ['DM_1' 'RUB_0'] |
| ['beta_blocker_therapy' 'calcium_channel_blocker' 'cbc' 'cmp' 'insulin' 'statin' 'sulfonylurea'] | ['DM_2' 'RUB_0'] |
| ['arb' 'metformin' 'sulfonylurea'] | ['DM_1' 'HF_1' 'RUB_0'] |
| ['dipeptidyl_peptidase_inhibitors' 'metformin'] | ['DM_1' 'HF_1' 'RUB_0'] |
| ['beta_blocker_therapy' 'calcium_channel_blocker' 'cbc' 'cmp' 'insulin' 'statin' 'sulfonylurea'] | ['DM_1' 'HF_1' 'RUB_0'] |
| ['dipeptidyl_peptidase_inhibitors' 'metformin'] | ['DM_1' 'HF_1' 'RUB_0'] |
| ['dipeptidyl_peptidase_inhibitors' 'metformin'] | ['DM_1' 'HF_1' 'RUB_0'] |
| ['beta_blocker_therapy' 'calcium_channel_blocker' 'cbc' 'cmp' 'insulin' 'statin' 'sulfonylurea'] | ['DM_1' 'HF_1' 'RUB_1'] |
| ['dipeptidyl_peptidase_inhibitors' 'metformin'] | ['DM_1' 'HF_1' 'RUB_0'] |
| ['dipeptidyl_peptidase_inhibitors' 'metformin'] | ['DM_1' 'HF_1' 'RUB_0'] |
| ['beta_blocker_therapy' 'calcium_channel_blocker' 'cbc' 'cmp' 'insulin' 'statin' 'sulfonylurea'] | ['DM_1' 'HF_1' 'RUB_0'] |

FIG. 6

MACHINE LEARNING TECHNIQUES FOR PREDICTIVE CLINICAL INTERVENTION RECOMMENDATION

BACKGROUND

Various embodiments of the present invention address technical challenges related to performing predictive data analysis operations and address the efficiency and reliability shortcomings of existing predictive data analysis solutions.

BRIEF SUMMARY

In general, embodiments of the present invention provide methods, apparatus, systems, computing devices, computing entities, and/or the like for perform predictive (e.g., prescriptive) data analysis operations. For example, certain embodiments of the present invention utilize systems, methods, and computer program products that perform predictive data analysis operations by using an agent machine learning model to determine an optimal clinical intervention based at least in part on the current clinical state and an inferred reinforcement learning policy that is determined based at least in part on a familiarity-adjusted reward function, where the familiarity-adjusted reward function is generated by an environment machine learning framework based at least in part on one or more next state predictions for one or more pruned action-state combinations based at least in part on a historical clinical outcome database, and the one or more pruned action-state combinations are determined based at least in part on one or more pruned clinical actions that are selected from a plurality of candidate clinical actions based at least in part on one or more action pruning criteria.

In accordance with one aspect, a method is provided. In one embodiment, the method comprises: determining, based at least in part on a current clinical state and using an agent machine learning model, an optimal clinical intervention, wherein: (i) the agent machine learning model is configured to determine the optimal clinical intervention based at least in part on the current clinical state and an inferred reinforcement learning policy that is determined based at least in part on a familiarity-adjusted reward function, (ii) the familiarity-adjusted reward function is generated by an environment machine learning framework based at least in part on one or more next state predictions for one or more pruned action-state combinations based at least in part on the historical clinical outcome database, and (iii) the one or more pruned action-state combinations are determined based at least in part on one or more pruned clinical actions that are selected from a plurality of candidate clinical actions based at least in part on one or more action pruning criteria; determining the clinical intervention recommendation based at least in part on the optimal clinical intervention; and performing one or more prediction-based actions based at least in part on the clinical intervention recommendation.

In accordance with another aspect, a computer program product is provided. The computer program product may comprise at least one computer-readable storage medium having computer-readable program code portions stored therein, the computer-readable program code portions comprising executable portions configured to: determine, based at least in part on a current clinical state and using an agent machine learning model, an optimal clinical intervention, wherein: (i) the agent machine learning model is configured to determine the optimal clinical intervention based at least in part on the current clinical state and an inferred reinforcement learning policy that is determined based at least in part on a familiarity-adjusted reward function, (ii) the familiarity-adjusted reward function is generated by an environment machine learning framework based at least in part on one or more next state predictions for one or more pruned action-state combinations based at least in part on the historical clinical outcome database, and (iii) the one or more pruned action-state combinations are determined based at least in part on one or more pruned clinical actions that are selected from a plurality of candidate clinical actions based at least in part on one or more action pruning criteria; determine the clinical intervention recommendation based at least in part on the optimal clinical intervention; and perform one or more prediction-based actions based at least in part on the clinical intervention recommendation.

In accordance with yet another aspect, an apparatus comprising at least one processor and at least one memory including computer program code is provided. In one embodiment, the at least one memory and the computer program code may be configured to, with the processor, cause the apparatus to: determine, based at least in part on a current clinical state and using an agent machine learning model, an optimal clinical intervention, wherein: (i) the agent machine learning model is configured to determine the optimal clinical intervention based at least in part on the current clinical state and an inferred reinforcement learning policy that is determined based at least in part on a familiarity-adjusted reward function, (ii) the familiarity-adjusted reward function is generated by an environment machine learning framework based at least in part on one or more next state predictions for one or more pruned action-state combinations based at least in part on the historical clinical outcome database, and (iii) the one or more pruned action-state combinations are determined based at least in part on one or more pruned clinical actions that are selected from a plurality of candidate clinical actions based at least in part on one or more action pruning criteria; determine the clinical intervention recommendation based at least in part on the optimal clinical intervention; and perform one or more prediction-based actions based at least in part on the clinical intervention recommendation.

BRIEF DESCRIPTION OF THE DRAWINGS

Figure 1:
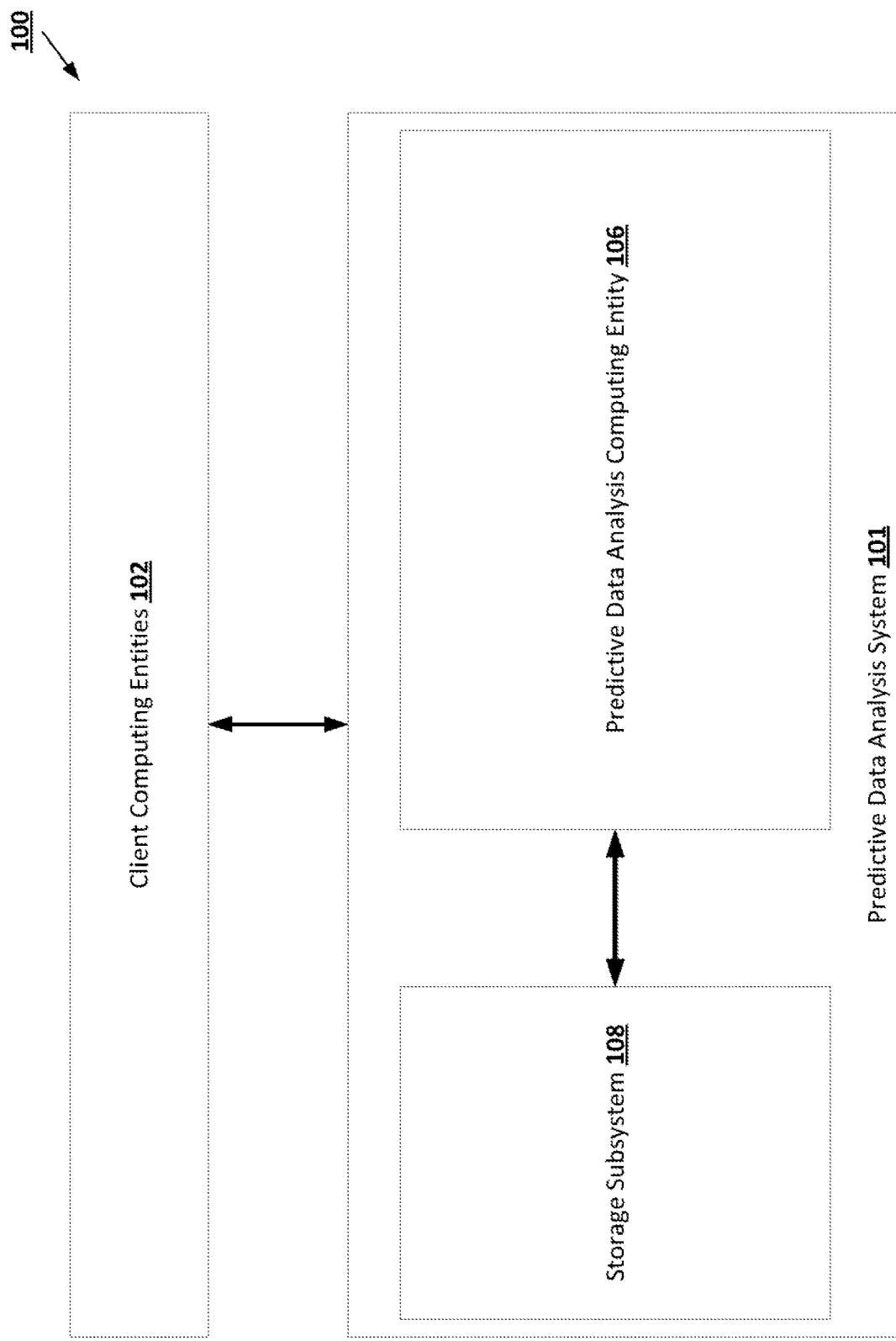

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
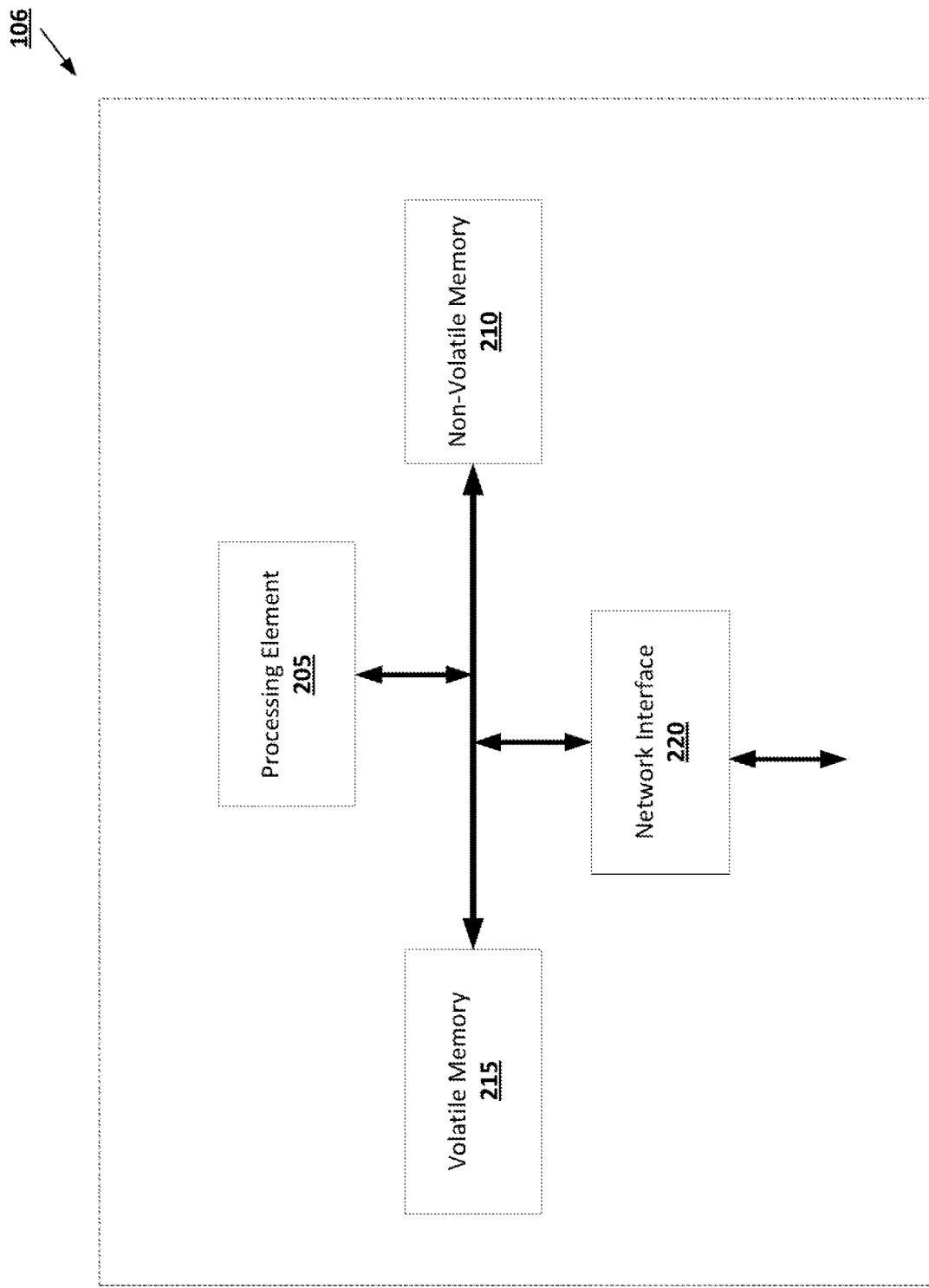

FIG. 2 provides an example predictive data analysis computing entity in accordance with some embodiments discussed herein.

Figure 3:
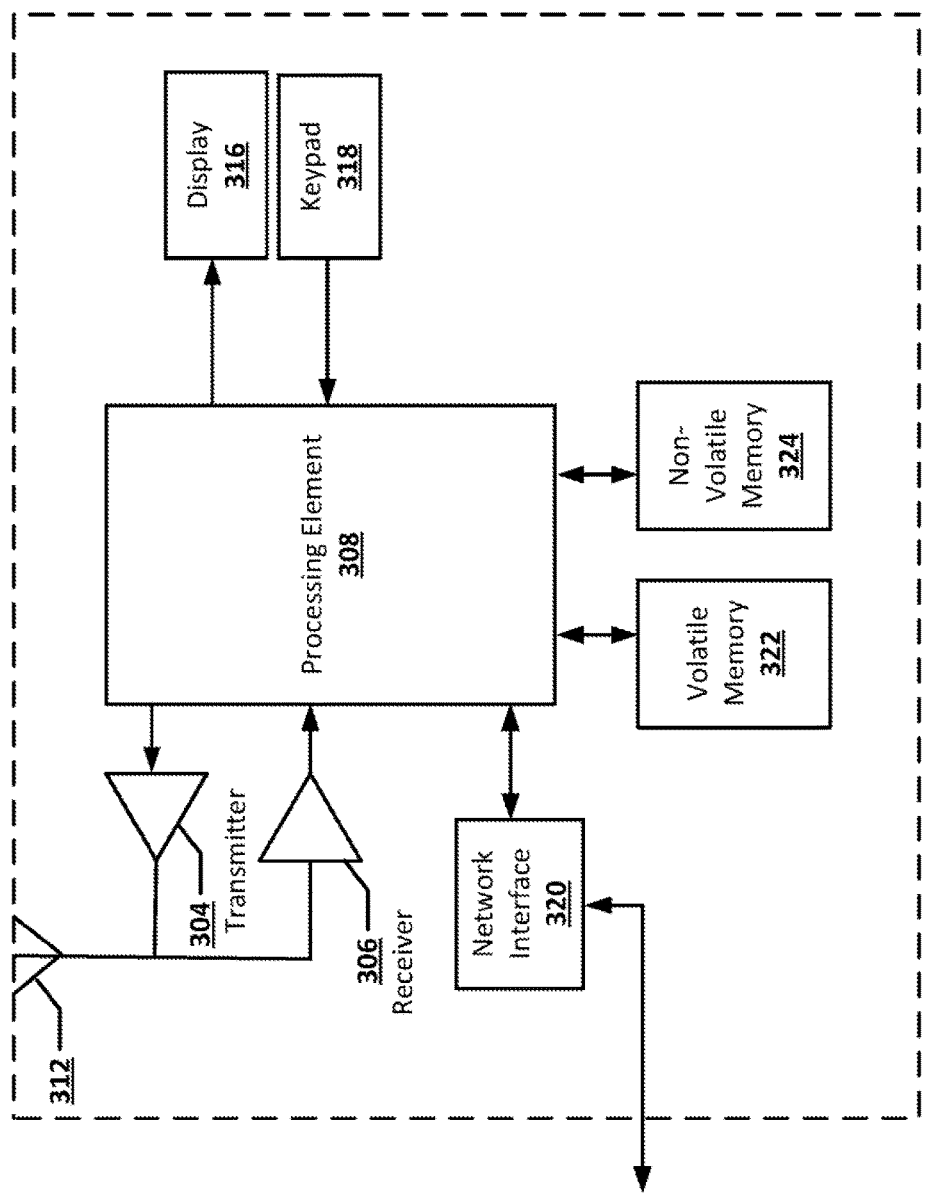

FIG. 3 provides an example client computing entity in accordance with some embodiments discussed herein.

Figure 4:
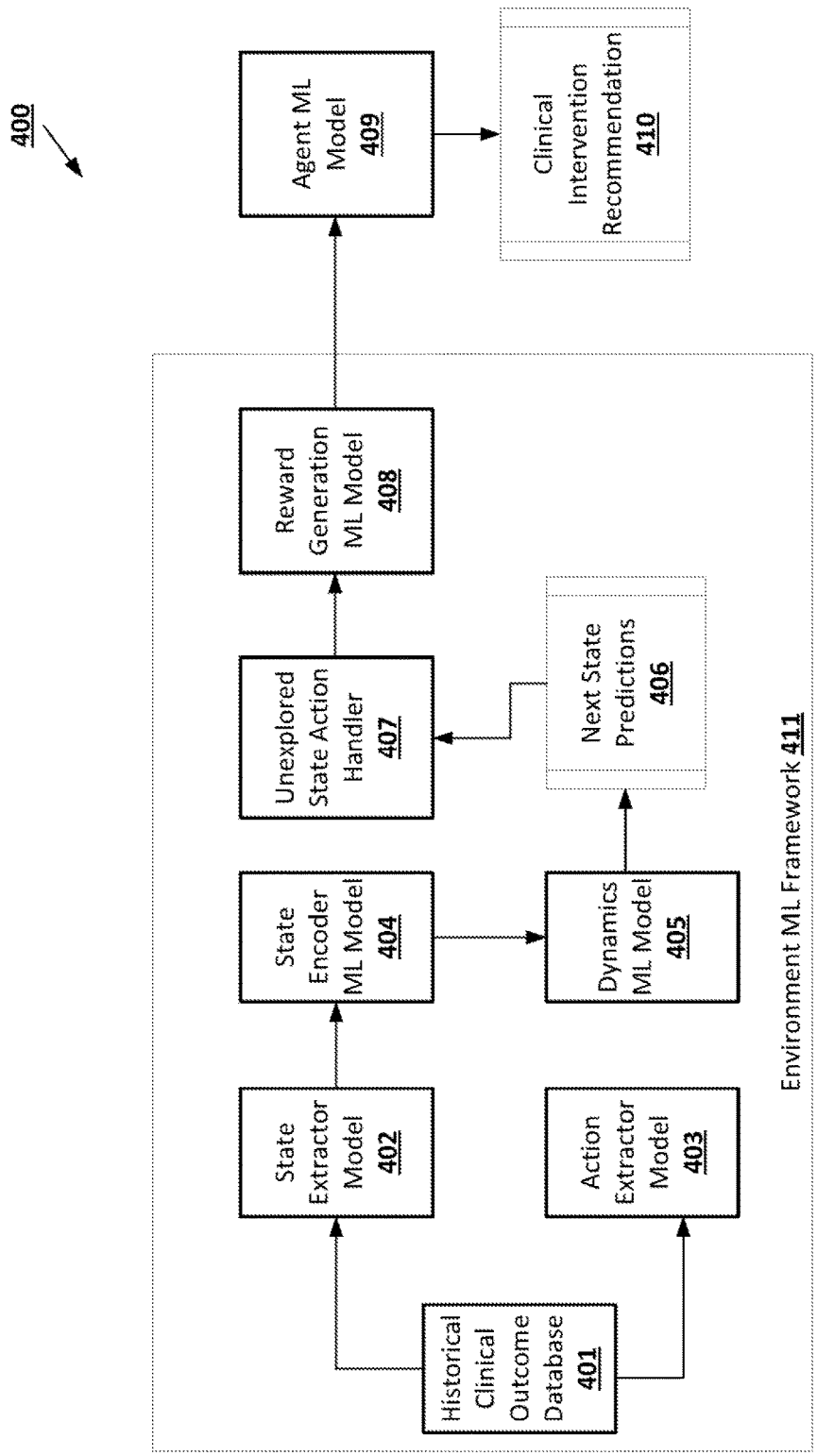

FIG. 4 is a data flow diagram of an example process for generating a clinical intervention recommendation given a current clinical state in accordance with some embodiments discussed herein.

Figure 5:
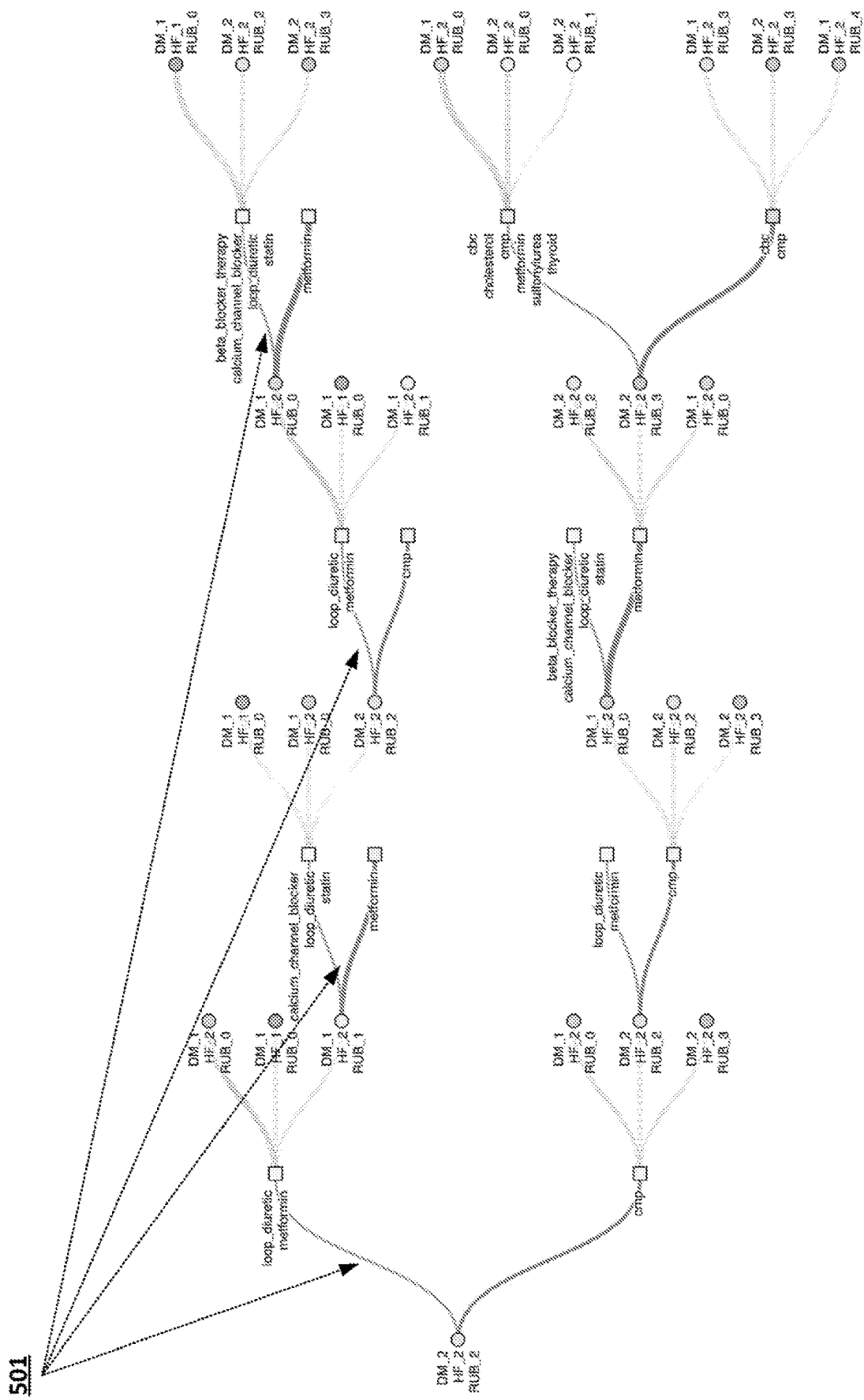

FIG. 5 provides an operational example of generating a clinical intervention recommendation in accordance with some embodiments discussed herein.

FIG. 6 provides an operational example of a prediction output user interface in accordance with some embodiments discussed herein.

Figure 7:
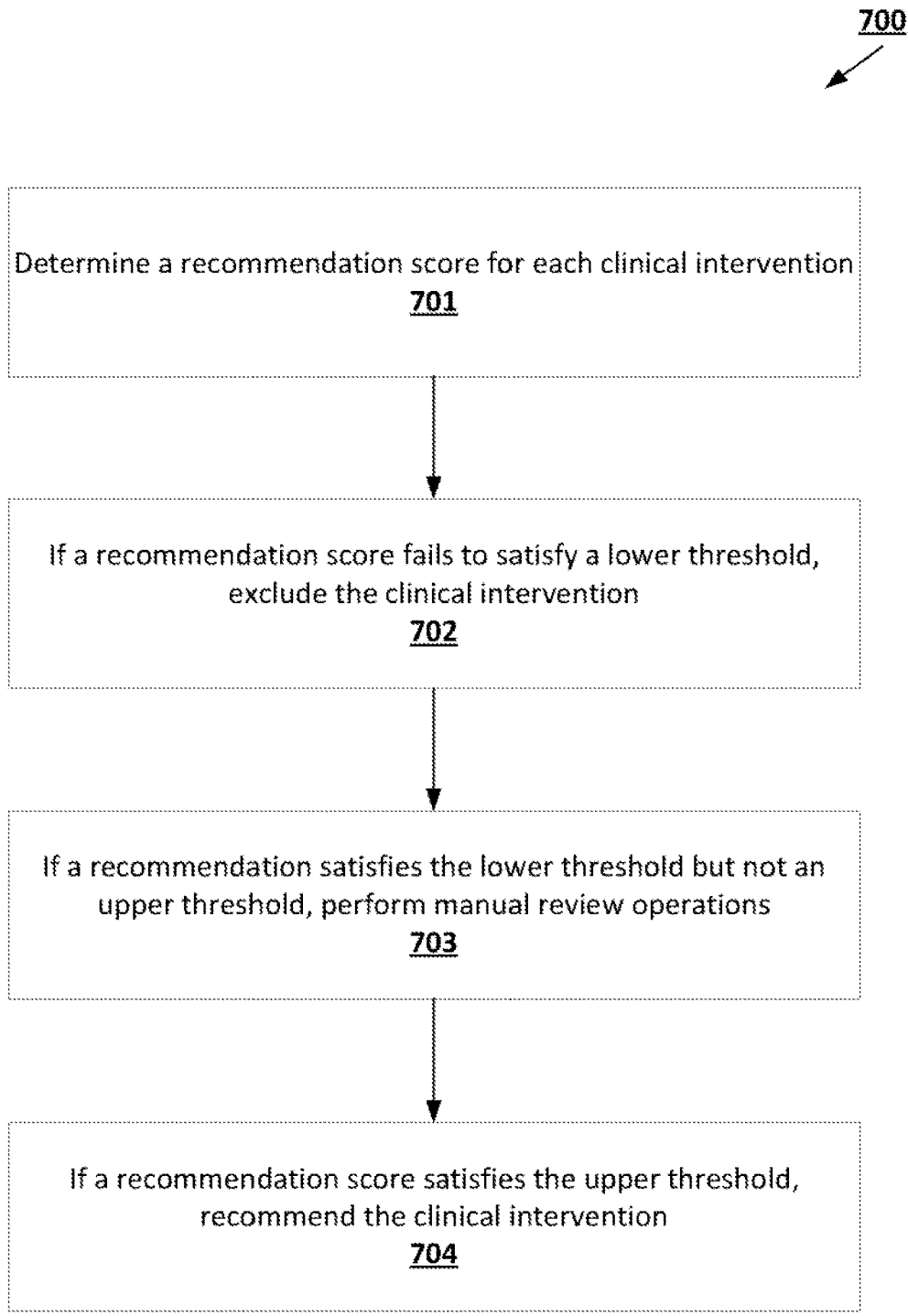

FIG. 7 is a flowchart diagram of an example process for performing a recommendation-based actions based at least in part on a clinical intervention recommendation in accordance with some embodiments discussed herein.

DETAILED DESCRIPTION

Various embodiments of the present invention now will be described more fully hereinafter with reference to the accompanying drawings, in which some, but not all, embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis tasks.

I. Overview and Technical Improvements

Various embodiments of the present invention address operational efficiency and operational reliability of predictive data analysis systems that are configured to perform predictive data analysis operations to generate clinical intervention recommendations. For example, various embodiments of the present invention improve accuracy of predictive outputs generated based at least in part on clinical intervention recommendations by using an agent machine learning model to determine an optimal clinical intervention based at least in part on the current clinical state and an inferred reinforcement learning policy that is determined based at least in part on a familiarity-adjusted reward function, where the familiarity-adjusted reward function is generated by an environment machine learning framework based at least in part on one or more next state predictions for one or more pruned action-state combinations based at least in part on a historical clinical outcome database, and the one or more pruned action-state combinations are determined based at least in part on one or more pruned clinical actions that are selected from a plurality of candidate clinical actions based at least in part on one or more action pruning criteria. Improving accuracy of the noted predictive outputs in turn: (i) decreases the number of computational operations performed by processing units of predictive data analysis systems, thus increasing the computational efficiency of predictive data analysis systems, (ii) decreases the overall likelihood of system failure given a constant per-recommendation likelihood failure, thus increasing operational reliability of predictive data analysis systems, and (iii) increases the overall number of end-users that the predictive data analysis system can serve given a constant per-user query count, thus increasing the operational throughput of predictive data analysis systems. Accordingly, various embodiments of the present disclosure make important technical contributions to the field of predictive data analysis by improving computational efficiency, operational reliability, and operational throughput of predictive data analysis systems.

An exemplary application of various embodiments of the present invention relate to a system to address a core problem of clinical diagnostics and prediction: namely, the ability to cross-reference clinical decision-making logic when describing the next best clinical action for a patient's given health status at a point in time. Clinical care is most often described using clinical decision trees, in which each condition is described using a single branching tree operating independently and asynchronously from other trees. A human physician or care provider is required to synthesize the decision trees and judge the next best action for that patient at each time. Human judgement is prone to bias, oversight, and variation in quality over time. Aspects of the Pathfinder concepts provide clinical decision support solutions that enable the physician to focus on interacting with the patient, while scanning all available clinical possibilities to determine an optimal care pathway.

II. Definitions

The term "historical clinical outcome database" may refer to a data construct that describes a collection of one or more historical experience records, where each historical experience record describes that a recorded performance of a pruned clinical action at a first defined clinical state has led to a second defined clinical state which may or may not be different than the first defined clinical state. In some embodiments, each historical experience record may have the form $(s_t, a_t, s_{t+1})$, where $s_t$ is the defined clinical state that is recorded to have occurred at time t, $a_t$ is a pruned clinical action that is recorded to have been taken at time t, and $s_{t+1}$ is a defined clinical state that is recorded to have occurred at a subsequent time after t after performance of the pruned clinical action at. In some embodiments, a dynamics machine learning model is trained based at least in part on ground-truth next state predictions described by the historical experience records that are determined based at least in part on the historical clinical outcome database. For example, given a historical experience record $(s_t, a_t, s_{t+1})$, the following training operation may be performed to generate/update the dynamics machine learning model: (i) $s_t$ and $a_t$ are processed by the dynamics machine learning model to generate a predicted next state prediction $s_{t+1}'$, (ii) an error function is determined based at least in part on a measure of error between the predicted $s_{t+1}'$ and the ground-truth $s_{t+1}$, and (iii) trainable parameters of the dynamics machine learning model are updated to minimize (e.g., locally minimize, globally minimize, and/or the like) the error function.

The term "clinical feature" may refer to a data construct that describes a feature of a clinical scenario that can be used to infer a clinical state for the clinical scenario. Examples of clinical features that can be used to generate clinical states include clinical features describing severity levels for conditions of interest, clinical features describing resource utilization levels over defined time periods, clinical features describing the number of organs being treated, clinical features describing specialties of recently visited providers, clinical features describing trajectories of utilization over the last N weeks, clinical features describing trajectories of severity levels over the last N weeks, clinical features describing sites of care, clinical features describing time from a last-recorded service, clinical features describing social determinants of health that are likely to affect long-term prognosis, clinical features describing behavioral determinants of health that are likely to affect the ability to achieve health goals, and/or the like.

The term "defined clinical state" may refer to a data construct that describes a combination of clinical feature values for a set of clinical features that describe a state of a clinical scenario that is associated with the noted clinical feature values. In some embodiments, a state extractor model is configured to: (i) identify a set of clinical features each having a set of clinical feature values based at least in part on a historical clinical outcome database, and (ii) generate the set of defined clinical states based at least in part on combinations of the clinical feature values across the clinical features. For example, if the set of clinical features include three features, where a first clinical feature is associated with a clinical feature values, a second clinical feature is associated with b clinical feature values, and a third clinical feature is associated with c clinical feature values, then the set of defined clinical states may include a*b*c defined clinical states. In some embodiments, for each defined clinical state, the state extractor model may generate a clinical state representation (e.g., using a one-hot-coded representation scheme).

The term "pruned clinical condition" may refer to a data construct that describes a combination of available clinical interventions that satisfies one or more action pruning criteria. In some embodiments, an action extractor model is configured to: (i) identify a set of clinical interventions, and (ii) generate the set of pruned clinical actions as a subset of n-sized combinations of the set of clinical interventions as determined based at least in part on one or more action pruning criteria. In some embodiments, for each pruned clinical action, the state extractor model generates a clinical state representation (e.g., using a one-hot-coded representation scheme). Generally, given m clinical interventions, there may be $2^m$ potential clinical actions which could make processing of a resulting action space computationally resource-intensive for large values of m. To combat this problem, the action space is pruned by removing potential clinical actions corresponding to clinical intervention combinations that are deemed to be less desirable based at least in part on action pruning criteria.

The term "action pruning criterion" may refer to a data construct that describes a condition that, when satisfied by a clinical intervention combination causes the clinical intervention combination to be excluded from a set of pruned clinical actions that can be used along with a set of defined clinical states to generate a set of action-state recommendations. In some embodiments, a clinical action space is pruned by removing potential clinical actions corresponding to clinical intervention combinations that are deemed to be less desirable based at least in part on action pruning criteria. Examples of action pruning criteria include: (i) an action pruning criterion that describes that a clinical intervention combination is less desirable if one or more clinical guidelines describe that the combination is harmful/unfeasible/ineffective and is thus a "non-recommended action pattern," (ii) an action pruning criterion that describes that a clinical intervention recommendation is less desirable if a historical clinical outcome database describes that the combination has produced suboptimal results in the past and is thus a "suboptimal action pattern," (iii) an action pruning criterion that describes that a clinical intervention recommendation is less desirable if the historical clinical outcome database describes that the combination has not been used by a sufficient ratio of practitioners in the past and is thus an "non-utilized action pattern," (iv) an action pruning criterion that describes that a clinical intervention recommendation is less desirable if the combination includes at least one clinical intervention that is not available at a place of deployment of an agent machine learning model, and (v) an action pruning criterion that describes that a clinical intervention combination is less desirable if one or more clinical guidelines describe that the combination does not include any medically significant clinical interventions.

The term "state encoder machine learning model" may refer to a data construct that describes parameters, hyper-parameters, and/or defined operations of a machine learning model that is configured to process a defined clinical state (and/or the state representation of the defined clinical state) to generate a clinical state encoding for the defined clinical state. In some embodiments, the state encoder machine learning model is configured to: (i) extract one or more defined clinical states based at least in part on a historical clinical outcome database, and (ii) for each defined clinical state, generate a clinical state encoding. In some embodiments, the state encoder machine learning model is an encoder component of an overall model that is trained as an encoder-decoder framework. In some embodiments, the state encoder machine learning model comprises an autoencoder machine learning model. In some embodiments, inputs to a state encoder machine learning model include a vector describing the state representation of an input clinical state, while outputs of a state encoder machine learning model include a vector describing a clinical state encoding of the input clinical state that is generated based at least in part on the state representation of the input clinical state.

The term "dynamics machine learning model" may refer to a data construct that describes parameters, hyper-parameters, and/or defined operations of a machine learning model that is configured to generate a next state prediction for each pruned action-state combination that is with a defined clinical state and a pruned clinical action. The dynamics machine learning model may be associated to process the action representation for a pruned clinical action of an action-state combination and a state representation for a defined clinical state of the action-state combination in order to generate a next state prediction for the action-state combination that describes a predicted future defined clinical state of an agent if the pruned clinical action is performed at the defined clinical state. The dynamics machine learning model may be trained based at least in part on state transitions defined by the historical clinical outcome database. In some embodiments, the dynamics machine learning model includes at least one of a feed forward neural network or a recurrent neural network (such as a long short term memory neural network, one-dimensional convolutional neural network, etc.) or even a polynomial function in the states and actions which outputs a state. In some embodiments, the dynamics machine learning model is configured to generate n likelihood scores, where n is the number of defined health states. In some embodiments, when the dynamics machine learning model is a feed forward neural network machine learning model, each likelihood score generated by the dynamics machine learning model describes a predicted likelihood that performance of an input pruned clinical action at an input defined clinical state will lead to the occurrence of a defined clinical state that is associated with the likelihood scores. In some embodiments, when the dynamics machine learning model is a recurrent neural network machine learning model, each likelihood score generated by the dynamics machine learning model describes a predicted likelihood that performance of a sequence of input pruned action-state combinations each associated with a defined clinical state and a pruned clinical action will lead to the occurrence of a defined clinical state that is associated with the likelihood scores. In both of the noted embodiments, given n likelihood scores generated by the dynamics machine learning model where each likelihood score is associated with a respective defined clinical state of n defined clinical states, the next state prediction is selected based at least in part on a defined clinical state of the n defined clinical states that has a highest likelihood score of the n likelihood scores. In some embodiments, if the dynamics machine learning model is a feed forward neural network machine learning model, the dynamics machine learning model is trained using gradient descent with backpropagation. In some embodiments, if the dynamics machine learning model is a recurrent neural network machine learning model, the dynamics machine learning model is trained using gradient descent with backpropagation through time. In some embodiments, inputs to a dynamics machine learning model include one or more vectors describing clinical state encodings and/or one or more vectors describing action representations. In some embodiments, outputs of a dynamics machine learning model include a vector that describes n likelihood scores as described above.

The term "unexplored state action handler" may refer to a data construct that describes a sequence of steps an algorithm that is configured to intelligently handle a next state predictions generated by a dynamics machine learning model to generate a familiarity-adjusted reward measure for each pruned action-state combination. The handler may be configured to generate a familiarity-adjusted reward measure for each pruned action-state combination based at least in part on the next-state prediction and an unfamiliarity measure for the pruned action-state combination that is determined based at least in part on an occurrence rate of the pruned action-state combination across the historical clinical outcome database. Exemplary techniques involving identifying and penalizing states and actions which have not been explored previously as a function of their distance from previously visited states are used in such systems and described for example in Kidambi et al., MOReL: *Model-Based Offline Reinforcement Learning* (2020), available online at https://arxiv.org/pdf/2005.05951.pdf. In some embodiments, although the dynamics machine learning model may be trained exclusively on data from the historical clinical outcome database which may include historical experience records corresponding to not but all of defined action-state combinations, once trained the dynamics machine learning model can generate next state predictions for all action-state combinations regardless of how often those action-state combinations occur in the training data that was used to generate the dynamics machine learning model. However, the next state predictions of the dynamics machine learning model for those action-state combinations that have a lower occurrence rate among the historical experience records of the historical clinical outcome database may be less reliable than those action-state combinations that have a higher occurrence rate among the historical experience records of the historical clinical outcome database. Accordingly, one objective of the handler is to reward or penalize performance of a clinical action $a_t$ at a defined clinical state $s_t$ based at least in part on occurrence rate of historical experience records having the form $(s_t, a_t, s_{t+1})$, where $s_{t+1}$ may be any resulting defined clinical state that is recorded to have occurred at a time t+1 after performing of the clinical action $a_t$ at time t given occurrence of the clinical state $s_t$ at time t. To do so, given a next state prediction for an action-state combination, the unexplored state action handler may adjust an initial reward measure for the clinical state described by the next state prediction with an unfamiliarity measure that is determined based at least in part on an occurrence rate of the action-state combination across the historical clinical outcome database (e.g., that is determined based at least in part on an inverse of the occurrence rate of the action-state combination across the historical clinical outcome database). In some embodiments, inputs to the handler include a vector describing a next state prediction for a state-action combination, while outputs include a vector and/or an atomic value describing a reward measure for the state-action combination.

The term "reward generation machine learning model" may refer to a data construct that describes parameters, hyper-parameters, and/or defined operations of a machine learning model that is configured to generate a familiarity-adjusted reward function based at least in part on each familiarity-adjusted reward measure. The reward generation machine learning model may comprise at least one of one or more rule-based machine learning layers and/or one or more trained machine learning layers. The reward generation machine learning model may be configured to generate a familiarity-adjusted reward function by combining each familiarity-adjusted reward measure for a pruned action-state combination. In some embodiments, the reward generation machine learning model is configured to generate a reinforcement learning policy based at least in part on the familiarity-adjusted reward function. In some embodiments, the reward generation machine learning model is the model inside the environment that returns reward given a current state and action, i.e., returns R(S,A). In some embodiments, this model is trained based at least in part on a historical database or a rule-based-heuristic, and takes state/action as input and produces a reward based at least in part on the noted input.

The term "agent machine learning model" may refer to a data construct that describes parameters, hyper-parameters, and/or defined operations of a machine learning model that is configured to process a current clinical state using the familiarity-adjusted reward function (e.g., using a reinforcement learning policy that is generated based at least in part on familiarity-adjusted reward function) to generate the clinical intervention recommendation for the current clinical state. The current clinical state is a defined clinical state that is detected to be present at a current time. In some embodiments, the inputs to the agent machine learning model include a 5-tuple $M=(S,A,P,R,\gamma)$, where: (i) S is an infinite or finite state space and $s_t \in S$ denotes the state of an agent at time t, (ii) A is a set of actions available to the agent and $a_t \in A$ denotes the action that the agent performs at time t, (iii) P is a transition function (also called dynamics) that describes when the agent transits from state s to state s' after taking action a (e.g., such that $P(s,a,s'):S \times A \times S' \to [0,1]$), (iv) R is a reward function that returns the immediate reward R(s,a) to the agent after taking action a in state s (e.g., such that $S \times A \to R$), and (v) $\gamma \in [0, 1]$ is a discount factor representing the discounting of time steps in the future and increases as time from point 0 increases. In some embodiments, the reinforcement learning policy used by the agent machine learning model (i.e., policy $\pi:S \times A \to [0,1]$) is a probability distribution that maps an action $a \in A$ to a state $s \in S$. In some embodiments, given a decision process (learned from real-world evidence) and a policy (defined above), the agent machine learning model computes an expected long-term benefit from state s is called the value of the policy, V (s).

III. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations. Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. Exemplary System Architecture

FIG. 1 is a schematic diagram of an example architecture 100 for performing predictive data analysis. The architecture 100 includes a predictive data analysis system 101 configured to receive predictive data analysis requests from client computing entities 102, process the predictive data analysis requests to generate predictions, provide the generated predictions to the client computing entities 102, and automatically perform prediction-based actions based at least in part on the generated predictions. An example of a prediction-based action that can be performed using the predictive data analysis system 101 is generating a clinical intervention recommendation for a patient/member.

In some embodiments, predictive data analysis system 101 may communicate with at least one of the client computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The predictive data analysis system 101 may include a predictive data analysis computing entity 106 and a storage subsystem 108. The predictive data analysis computing entity 106 may be configured to receive predictive data analysis requests from one or more client computing entities 102, process the predictive data analysis requests to generate predictions corresponding to the predictive data analysis requests, provide the generated predictions to the client computing entities 102, and automatically perform prediction-based actions based at least in part on the generated predictions.

The storage subsystem 108 may be configured to store input data used by the predictive data analysis computing entity 106 to perform predictive data analysis as well as model definition data used by the predictive data analysis computing entity 106 to perform various predictive data analysis tasks. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include, or be in communication with, one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further include, or be in communication with, non-volatile media (also referred to as non-volatile storage, memory, memory storage, memory circuitry and/or similar terms used herein interchangeably). In one embodiment, the non-volatile storage or memory may include one or more non-volatile storage or memory media 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the predictive data analysis computing entity 106 may further include, or be in communication with, volatile media (also referred to as volatile storage, memory, memory storage, memory circuitry and/or similar terms used herein interchangeably). In one embodiment, the volatile storage or memory may also include one or more volatile storage or memory media 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include, or be in communication with, one or more input elements, such as a keyboard input, a mouse input, a touch screen/display input, motion input, movement input, audio input, pointing device input, joystick input, keypad input, and/or the like. The predictive data analysis computing entity 106 may also include, or be in communication with, one or more output elements (not shown), such as audio output, video output, screen/display output, motion output, movement output, and/or the like.

Exemplary Client Computing Entity

FIG. 3 provides an illustrative schematic representative of an client computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 102 can be operated by various parties. As shown in FIG. 3, the client computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the predictive data analysis computing entity 106. In a particular embodiment, the client computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the predictive data analysis computing entity 106 via a network interface 320.

Via these communication standards and protocols, the client computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 102 can also download changes, add-ons, and updates, for instance, to its firmware, software (e.g., including executable instructions, applications, program modules), and operating system.

According to one embodiment, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the client computing entity's 102 position in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The client computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the client computing entity 102 to interact with and/or cause display of information/data from the predictive data analysis computing entity 106, as described herein. The user input interface can comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the client computing entity 102. As indicated, this may include a user application that is resident on the entity or accessible through a browser or other user interface for communicating with the predictive data analysis computing entity 106 and/or various other computing entities.

In another embodiment, the client computing entity 102 may include one or more components or functionality that are the same or similar to those of the predictive data analysis computing entity 106, as described in greater detail above. As will be recognized, these architectures and descriptions are provided for exemplary purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. Exemplary System Operations

As described below, various embodiments of the present invention address operational efficiency and operational reliability of predictive data analysis systems that are configured to perform predictive data analysis operations to generate clinical intervention recommendations. For example, various embodiments of the present invention improve accuracy of predictive outputs generated based at least in part on clinical intervention recommendations by using an agent machine learning model to determine an optimal clinical intervention based at least in part on the current clinical state and an inferred reinforcement learning policy that is determined based at least in part on a familiarity-adjusted reward function, where the familiarity-adjusted reward function is generated by an environment machine learning framework based at least in part on one or more next state predictions for one or more pruned action-state combinations based at least in part on a historical clinical outcome database, and the one or more pruned action-state combinations are determined based at least in part on one or more pruned clinical actions that are selected from a plurality of candidate clinical actions based at least in part on one or more action pruning criteria. Improving accuracy of the noted predictive outputs in turn: (i) decreases the number of computational operations performed by processing units of predictive data analysis systems, thus increasing the computational efficiency of predictive data analysis systems, (ii) decreases the overall likelihood of system failure given a constant per-recommendation likelihood failure, thus increasing operational reliability of predictive data analysis systems, and (iii) increases the overall number of end-users that the predictive data analysis system can serve given a constant per-user query count, thus increasing the operational throughput of predictive data analysis systems. Accordingly, various embodiments of the present disclosure make important technical contributions to the field of predictive data analysis by improving computational efficiency, operational reliability, and operational throughput of predictive data analysis systems.

FIG. 4 is a data flow diagram of an example process 400 for generating a clinical intervention recommendation 410 given a current clinical state. Via the various steps/operations of the process 400, the predictive data analysis computing entity 106 can use an inferred reward function that is generated based at least in part on a historical clinical outcome database 401 to generate a familiarity-adjusted reward function that can then be used by an agent machine learning model 409 to generate the clinical intervention recommendation 410.

However, while the various embodiments of the present invention depict that all of the steps/operations of the process 400 are performed by a single computing entity, a person of ordinary skill in the relevant technology will recognize that n subsets of steps/operations of the process 400 may be performed by up to n computing entities (e.g., up to n distributed computing entities). For example, in some embodiments, the operations of the environment machine learning framework 411 may be performed by a first computing entity and the operations of the agent machine learning model 409 may be performed by a second computing entity that is distinct from (e.g., is remotely located relative to) the first computing entity.

The process 400 begins when a state extractor model 402 of the environment machine learning framework 411 generates a set of defined clinical states based at least in part on the historical clinical outcome database 401. The state extractor model 402 may be configured to: (i) identify a set of clinical features each having a set of clinical feature values based at least in part on the historical clinical outcome database 401, and (ii) generate the set of defined clinical states based at least in part on combinations of the clinical feature values across the clinical features. For example, if the set of clinical features include three features, where a first clinical feature is associated with a clinical feature values, a second clinical feature is associated with b clinical feature values, and a third clinical feature is associated with c clinical feature values, then the set of defined clinical states may include a*b*c defined clinical states. In some embodiments, for each defined clinical state, the state extractor model 402 generates a clinical state representation (e.g., using a one-hot-coded representation scheme).

Examples of clinical features that can be used to generate clinical states include clinical features describing severity levels for conditions of interest, clinical features describing resource utilization levels over defined time periods, clinical features describing the number of organs being treated, clinical features describing specialties of recently visited providers, clinical features describing trajectories of utilization over the last N weeks, clinical features describing trajectories of severity levels over the last N weeks, clinical features describing sites of care, clinical features describing time from a last-recorded service, clinical features describing social determinants of health that are likely to affect long-term prognosis, clinical features describing behavioral determinants of health that are likely to affect the ability to achieve health goals, and/or the like.

The process 400 further comprises using an action extractor model 403 of the environment machine learning framework 411 to generate a set of pruned clinical actions based at least in part on the historical clinical outcome database 401. In some embodiments, the action extractor model 403 is configured to: (i) identify a set of clinical interventions, and (ii) generate the set of pruned clinical actions as a subset of n-sized combinations of the set of clinical interventions as determined based at least in part on one or more action pruning criteria. In some embodiments, for each pruned clinical action, the action extractor model 403 generates a clinical state representation (e.g., using a one-hot-coded representation scheme).

Generally, given m clinical interventions, there may be $2^m$ potential clinical actions which could make processing of a resulting action space computationally resource-intensive for large values of m. To combat this problem, the action space is pruned by removing potential clinical actions corresponding to clinical intervention combinations that are deemed to be less desirable based at least in part on action pruning criteria.

Examples of action pruning criteria include: (i) an action pruning criterion that describes that a clinical intervention combination is less desirable if one or more clinical guidelines describe that the combination is harmful/unfeasible/ineffective and is thus a "non-recommended action pattern," (ii) an action pruning criterion that describes that a clinical intervention recommendation is less desirable if the historical clinical outcome database 401 describes that the combination has produced suboptimal results in the past and is thus a "suboptimal action pattern," (iii) an action pruning criterion that describes that a clinical intervention recommendation is less desirable if the historical clinical outcome database 401 describes that the combination has not been used by a sufficient ratio of practitioners in the past and is thus an "non-utilized action pattern," (iv) an action pruning criterion that describes that a clinical intervention recommendation is less desirable if the combination includes at least one clinical intervention that is not available at a place of deployment of the agent machine learning model 409, and (v) an action pruning criterion that describes that a clinical intervention combination is less desirable if one or more clinical guidelines describe that the combination does not include any medically significant clinical interventions.

The process 400 continues when a state encoder machine learning model 404 of the environment machine learning framework 411 processes each defined clinical state (and/or the state representation of each defined clinical state) to generate a clinical state encoding for the defined clinical state. In some embodiments, the state encoder machine learning model 404 is configured to: (i) extract one or more defined clinical states based at least in part on the historical clinical outcome database 401, and (ii) for each defined clinical state, generate a clinical state encoding. In some embodiments, the state encoder machine learning model 404 is an encoder component of an overall model that is trained as an encoder-decoder framework. In some embodiments, the state encoder machine learning model 404 comprises an autoencoder machine learning model.

The process 400 continues when a dynamics machine learning model 405 of the environment machine learning framework 411 generates a next state prediction 406 for each pruned action-state combination that is associated with a defined clinical state and a pruned clinical action. The dynamics machine learning model 405 may be associated to process the action representation for a pruned clinical action of an action-state combination and a state representation for a defined clinical state of the action-state combination in order to generate a next state prediction for the action-state combination that describes a predicted future defined clinical state of an agent if the pruned clinical action is performed at the defined clinical state. The dynamics machine learning model 405 may be trained based at least in part on state transitions defined by the historical clinical outcome database 401. In some embodiments, the dynamics machine learning model 405 includes at least one of a feed forward neural network or a recurrent neural network (such as a long short term memory neural network).

In some embodiments, the historical clinical outcome database 401 is configured to describe various historical experience records, where each historical experience record describes that a recorded performance of a pruned clinical action at a first defined clinical state has led to a second defined clinical state which may or may not be different than the first defined clinical state. In some embodiments, each historical experience record may have the form $(s_t, a_t, s_{t+1})$, where $s_t$ is the defined clinical state that is recorded to have occurred at time t, $a_t$ is a pruned clinical action that is recorded to have been taken at time t, and $s_{t+1}$ is a defined clinical state that is recorded to have occurred at a subsequent time after t after performance of the pruned clinical action at.

In some embodiments, the dynamics machine learning model 405 is configured to generate n likelihood scores, where n is the number of defined health states. In some embodiments, when the dynamics machine learning model 405 is a feed forward neural network machine learning model, each likelihood score generated by the dynamics machine learning model 405 describes a predicted likelihood that performance of an input pruned clinical action at an input defined clinical state will lead to the occurrence of a defined clinical state that is associated with the likelihood scores.

In some embodiments, when the dynamics machine learning model 405 is a recurrent neural network machine learning model, each likelihood score generated by the dynamics machine learning model 405 describes a predicted likelihood that performance of a sequence of input pruned action-state combinations each associated with a defined clinical state and a pruned clinical action will lead to the occurrence of a defined clinical state that is associated with the likelihood scores. In both of the noted embodiments, given n likelihood scores generated by the dynamics machine learning model 405 where each likelihood score is associated with a respective defined clinical state of n defined clinical states, the next state prediction 406 is selected based at least in part on a defined clinical state of the n defined clinical states that has a highest likelihood score of the n likelihood scores.

As described above, the dynamics machine learning model 405 may be a recurrent neural network machine learning model such as a long short term memory machine learning model. In some embodiments, when the dynamics machine learning model 405 is a recurrent neural network machine learning model, instead of generating a next state prediction 406 for a single action-state prediction, the dynamics machine learning model 405 may describe the next state prediction 406 for a sequence of consecutive q action-state combinations, where q may be a hyper-parameter of the recurrent neural network machine learning model. For example, given q=2, the input to the dynamics machine learning model 405 may include, for a first timestep, a state representation of a defined clinical state $s_{t-1}$ and a pruned clinical action $a_{t-1}$, and for a second timestep, a state representation of a defined clinical state $s_t$ and a pruned clinical action at.

In some embodiments, the dynamics machine learning model 405 is trained based at least in part on ground-truth next state predictions described by the historical experience records that are determined based at least in part on the historical clinical outcome database 401. For example, given a historical experience record $(s_t, a_t, s_{t+1})$, the following training operation may be performed to generate/update the dynamics machine learning model 405: (i) $s_t$ and $a_t$ are processed by the dynamics machine learning model 405 to generate a predicted next state prediction $s_{t+1}'$, (ii) an error function is determined based at least in part on a measure of error between the predicted $s_{t+1}'$ and the ground-truth $s_{t+1}$, and (iii) trainable parameters of the dynamics machine learning model 405 are updated to minimize (e.g., locally minimize, globally minimize, and/or the like) the error function.

In some embodiments, if the dynamics machine learning model 405 is a feed forward neural network machine learning model, the dynamics machine learning model 405 is trained using gradient descent with backpropagation. In some embodiments, if the dynamics machine learning model 405 is a recurrent neural network machine learning model, the dynamics machine learning model 405 may be trained using gradient descent with backpropagation through time. If the dynamics model is a polynomial logit function, the weights are trained using techniques such as maximum likelihood estimator. Exemplary techniques involving identifying and penalizing states and actions which have not been explored previously as a function of their distance from previously visited states are used in such systems and described for example in Kidambi et al., MOReL: *Model-Based Offline Reinforcement Learning* (2020), available online at https://arxiv.org/pdf/2005.05951.pdf.

The process 400 continues when the unexplored state action handler 407 of the environment machine learning framework 411 processes the next state predictions 406 generated by the dynamics machine learning model 405 to generate a familiarity-adjusted reward measure for each pruned action-state combination.

The unexplored state action handler 407 may be configured to generate a familiarity-adjusted reward measure for each pruned action-state combination based at least in part on the next-state prediction and an unfamiliarity measure for the pruned action-state combination that is determined based at least in part on an occurrence rate of the pruned action-state combination across the historical clinical outcome database. Exemplary techniques involving identifying and penalizing states and actions which have not been explored previously as a function of their distance from previously visited states are used in such systems and described for example in Kidambi et al., MOReL: *Model-Based Offline Reinforcement Learning* (2020), available online at https://arxiv.org/pdf/2005.05951.pdf.

As described above, although the dynamics machine learning model 405 may be trained exclusively on data from the historical clinical outcome database 401 which may include historical experience records corresponding to not but all of defined action-state combinations, once trained the dynamics machine learning model 405 can generate next state predictions for all action-state combinations regardless of how often those action-state combinations occur in the training data that was used to generate the dynamics machine learning model 405. However, the next state predictions of the dynamics machine learning model 405 for those action-state combinations that have a lower occurrence rate among the historical experience records of the historical clinical outcome database 401 may be less reliable than those action-state combinations that have a higher occurrence rate among the historical experience records of the historical clinical outcome database 401.

Accordingly, one objective of the unexplored state action handler 407 may in some embodiments be to reward or penalize performance of a clinical action $a_t$ at a defined clinical state $s_t$ based at least in part on occurrence rate of historical experience records having the form $(s_t, a_t, s_{t+1})$, where $s_{t+1}$ may be any resulting defined clinical state that is recorded to have occurred at a time t+1 after performing of the clinical action $a_t$ at time t given occurrence of the clinical state $s_t$ at time t. To do so, given a next state prediction for an action-state combination, the unexplored state action handler 407 may adjust an initial reward measure for the clinical state described by the next state prediction with an unfamiliarity measure that is determined based at least in part on an occurrence rate of the action-state combination across the historical clinical outcome database (e.g., that is determined based at least in part on an inverse of the occurrence rate of the action-state combination across the historical clinical outcome database).

The process 400 continues when a reward generation machine learning model 408 of the environment machine learning framework 411 determines a familiarity-adjusted reward function based at least in part on each familiarity-adjusted reward measure generated by the unexplored state action handler 407. The reward generation machine learning model may comprise at least one of one or more rule-based machine learning layers and/or one or more trained machine learning layers. The reward generation machine learning model 408 may be configured to generate a familiarity-adjusted reward function by combining each familiarity-adjusted reward measure for a pruned action-state combination. In some embodiments, the reward generation machine learning model 408 is configured to generate a reinforcement learning policy based at least in part on the familiarity-adjusted reward function.

The process 400 continues when the agent machine learning model 409 processes a current clinical state using the familiarity-adjusted reward function (e.g., using a reinforcement learning policy that is generated based at least in part on familiarity-adjusted reward function) to generate the clinical intervention recommendation 410 for the current clinical state. The current clinical state is a defined clinical state that is detected to be present at a current time.

In some embodiments, the inputs to the agent machine learning model 409 include a 5-tupe M=(S,A,P,R,γ), where: (i) S is a finite state space and $s_t \in S$ denotes the state of an agent at time t, (ii) A is a set of actions available to the agent and $a_t \in A$ denotes the action that the agent performs at time t, (iii) P is a transition function (also called a controller) that describes when the agent transits from state s to state s' after taking action a (e.g., such that $P(s,a,s'):S \times A \times S' \rightarrow [0,1]$), (iv) R is a reward function that returns the immediate reward R(s,a) to the agent after taking action a in state s (e.g., such that $S \times A \rightarrow R$), and (v) $\gamma \in [0,1]$ is a discount factor representing the discounting of time steps in the future and increases as time from point 0 increases. In some embodiments, the reinforcement learning policy used by the agent machine learning model 409 (i.e., policy $\pi: S \times A \rightarrow [0,1]$) is a probability distribution that maps an action $a \in A$ to a state $s \in S$. In some embodiments, given a decision process (learned from real-world evidence) and a policy (defined above), the agent machine learning model 409 computes an expected long-term benefit from state s is called the value of the policy, $V^\pi(s)$, which may be calculated using the equation $V^\pi(s)=R(s)+\gamma\Sigma P(s'|s,\pi(s))V^\pi(s')$.

In some embodiments, to generate the clinical intervention recommendation 410 for a current clinical state, the agent machine learning model 409 finds a plurality of clinical interventions (e.g., a sequence of clinical interventions) that optimize the output of the equation:

$$Q^*(s, a) = \mathcal{R}(s, a) + \gamma \sum_{s' \in \mathcal{S}} \mathcal{P}(s, a, s') \max_{a' \in \mathcal{A}} Q(s', a') \quad \text{Equation 1}$$

In some embodiments, if a provider provides one or more provider modifications to the sequence of clinical interventions (e.g., by indicating that, of the plurality of clinical interventions, some of the clinical interventions will not be adopted by the provider), the agent machine learning model 409 performs the following operations: (i) identifying a modified clinical intervention based at least in part on one or more provider modifications to the optimal clinical intervention; and (ii) determining, based at least in part on the familiarity-adjusted reward function and using the agent machine learning model, an updated clinical intervention recommendation that comprises a plurality of modified optimal clinical interventions beginning with the modified clinical intervention. In some embodiments, when the clinical intervention recommendation 410 includes a plurality of clinical interventions, each proposed optimal clinical intervention in the plurality of proposed optimal clinical interventions is associated with a predefined clinical recommendation score; and in response to determining that the predefined clinical recommendation score for a particular proposed optimal clinical intervention satisfies a lower threshold but fails to satisfy an upper threshold, one or more manual review operations are performed with respect to the proposed optimal clinical intervention. In some embodiments, the modified clinical intervention is determined based at least in part on optimality criteria selected based at least in part on patient preference (e.g., as indicated via communications between the physician and the patient).

As noted above, in some embodiments, the clinical intervention recommendation 410 includes a sequence of clinical interventions that are recommended based at least in part on the clinical intervention recommendation 410. An operational example of such a clinical intervention recommendation 410 is depicted in FIG. 5. As depicted in FIG. 5, the clinical intervention recommendation 410 includes clinical intervention described along the pathway 501, which includes: loop diuretic and metformin, followed by calcium channel blocker, loop diuretic, and statin, followed by loop diuretic and metformin, and followed by beta blocker therapy, calcium channel blocker, loop diuretic, and statin. In the operational example of FIG. 5, if the provider indicates that he intends to prescribe Comprehensive Metabolic Panel (CMP) at first instead of loop diuretic and metformin as the first interventions, then the following clinical intervention recommendation 410 may alternatively be recommended: CMP, followed by medications, loop diuretic and metformin, followed by beta blocker therapy, calcium channel blocker, loop diuretic, and statin, and followed by cbc, cholesterol, metformin, sulfonylurea, and thyroid.

Accordingly, various embodiments of the present invention address operational efficiency and operational reliability of predictive data analysis systems that are configured to perform predictive data analysis operations to generate clinical intervention recommendations. For example, various embodiments of the present invention improve accuracy of predictive outputs generated based at least in part on clinical intervention recommendations by using an agent machine learning model to determine an optimal clinical intervention based at least in part on the current clinical state and an inferred reinforcement learning policy that is determined based at least in part on a familiarity-adjusted reward function, where the familiarity-adjusted reward function is generated by an environment machine learning framework based at least in part on one or more next state predictions for one or more pruned action-state combinations based at least in part on a historical clinical outcome database, and the one or more pruned action-state combinations are determined based at least in part on one or more pruned clinical actions that are selected from a plurality of candidate clinical actions based at least in part on one or more action pruning criteria. Improving accuracy of the noted predictive outputs in turn: (i) decreases the number of computational operations performed by processing units of predictive data analysis systems, thus increasing the computational efficiency of predictive data analysis systems, (ii) decreases the overall likelihood of system failure given a constant per-recommendation likelihood failure, thus increasing operational reliability of predictive data analysis systems, and (iii) increases the overall number of end-users that the predictive data analysis system can serve given a constant per-user query count, thus increasing the operational throughput of predictive data analysis systems. Accordingly, various embodiments of the present disclosure make important technical contributions to the field of predictive data analysis by improving computational efficiency, operational reliability, and operational throughput of predictive data analysis systems.

In some embodiments, the clinical intervention recommendation 410 is used to perform one or more prediction-based actions. Examples of prediction-based actions include automatically scheduling medical appointments corresponding to the clinical intervention recommendation 410 and/or automatically transmitting medication/treatment requests corresponding to the clinical intervention recommendation 410. In some embodiments, performing prediction-based actions includes generating user interface data for a prediction output user interface that is configured to display a sequence of recommended clinical interventions along with future clinical states that are predicted to result from performing the sequence of recommended clinical interventions. For example, as depicted in FIG. 6, the prediction output user interface 600 depicts that performing the recommended clinical interventions described in column 601 will lead to future clinical states described in column 602. In the prediction output user interface 600 of FIG. 6, the association of the recommended clinical interventions and the future clinical states shows that the recommended clinical interventions 611-612 should be performed in the same step of the sequence as they are associated with a common future clinical state 621.

In some embodiments, performing prediction-based actions based at least in part on the clinical intervention recommendation 410 may be performed in accordance with the process 700 that is depicted in FIG. 7. As depicted in FIG. 7, at step/operation 701, a recommendation score is generated for each clinical intervention of m potential clinical interventions based at least in part on correspondence of the potential clinical intervention to the clinical intervention recommendation 410. At step/operation 702, if the recommendation score for a potential clinical intervention fails to satisfy a lower threshold, then the potential clinical intervention is deemed harmful and/or ineffective and thus not recommended. At step/operation 703, if the recommendation score for a potential clinical intervention satisfies the lower threshold but not an upper threshold, then the potential clinical intervention is deemed potentially harmful and/or ineffective and thus not provided for manual review (e.g., by a provider profile, by an expert profile, and/or the like). At step/operation 704, if the recommendation score for a potential clinical intervention satisfies the upper threshold, then the potential clinical intervention is deemed non-harmful and/or effective and thus recommended as part of the predictive output provided to a query-initiating user profile (e.g., a query-initiating provider user profile).

In some embodiments, process 400 can be used to provide a system that scans the patient's medical history and unique combination of risk factors from their medical and claims history, as compared to other patients with a similar profile. The patient's specific clinical and claims profiles may be encoded into a representation layer of their health state at that specific point in time. The health state is represented in both time-dependent and time-agnostic layers, as well as with diagnosis-specific and diagnosis-agnostic features. Using trial-and-error prescriptive modeling that trials every possible combination of actions and action sequences, the system may be the sequence of actions that optimizes the health state at a user-designated time t, with the fewest actions. At this point, action sequences with poor outcomes at time t can be removed from consideration. This truncation of the action space at t0 effectively removes suboptimal future outcome variation in health state by removing the action sequences which arrive at those poor states. The system may recommend an optimal next step or series of steps. Optimization is defined as maximizing an individual's health outcomes—including mortality, disease progression, and acute utilization episodes. In some embodiments, the choice of which may depend on the age, familial situation of the patient, the optimal next step may be in terms of reducing the number of encounters with the healthcare system and/or, number of procedures. The system may be able to recommend a longer-term care plan, assuming perfect or imperfect adherence to the care pathway. Physicians, reviewers, or other users may choose the horizon of the care pathway they wish to generate, e.g., up to 18-24 months in the future.

In some embodiments, at the point of care, when a clinician is deciding on which course of treatment or next steps to take on behalf of a patient's care, the clinician will be able to access information containing Pathfinder's recommendations on care pathway. A proposed system may have access to the full suite of patient historical information and claims, so it is able to assist the physician in recommending or reducing actions that lead to poor outcomes. Clinicians may be able to choose from the list of recommended, on-guideline care actions and intermediate to long term care pathway plans to have those interventions automatically routed to the patient's insurance company for authorization or payment. Based at least in part on the procedures chosen by the provider (either on-pathway or off-pathway), the system may recalculate the individual's risk levels and future trajectory.

The above-described feedback loop may create real-time records of a patient's risk and most likely future utilization trajectory. This real-time information may be transmitted to primary care physicians (if rendering was specialist), other specialists or providers in the patient's care plan to ensure adequate coordination among care providers. Further, payer or provider care management teams may also receive the information if the patient is enrolled in a disease management program, and there exists risk that the patient is not receiving the personalized pathway-recommended care they need to improve their health state. If the clinician chooses not to choose from on-pathway individualized care, their action may be stratified as higher risk by Pathfinder. Higher risk action sequences may be routed to existing utilization management workflows.

In some embodiments, when a provider submits a claim or an authorization request for a service on behalf of a patient, a proposed system fits in to the existing workflow by stratifying higher risk claims and routing them to human examination, and automatically triaging low-risk, on-pathway claims to existing payment systems. After a claim or authorization has been generated by existing provider protocols, the proposed system has already scored the care pathway chosen by the provider. If the pathway is deemed guideline-based and evidence-based, then the auth is automatically approved or claim is routed to payment. If the pathway is deemed non-guideline based, then the claim or authorization is routed to increasingly skilled human reviewers who will ultimately make a pay/no-pay decision, and work with the provider to understand their care plan for the patient. If the care pathway is deemed highly non-standard vis-á-vis individualized guideline-based care recommendations, then the claim or auth may be routed to Fraud, Waste, and Abuse engines.

As described above, various embodiments of the present invention address operational efficiency and operational reliability of predictive data analysis systems that are configured to perform predictive data analysis operations to generate clinical intervention recommendations. For example, various embodiments of the present invention improve accuracy of predictive outputs generated based at least in part on clinical intervention recommendations by using an agent machine learning model to determine an optimal clinical intervention based at least in part on the current clinical state and an inferred reinforcement learning policy that is determined based at least in part on a familiarity-adjusted reward function, where the familiarity-adjusted reward function is generated by an environment machine learning framework based at least in part on one or more next state predictions for one or more pruned action-state combinations based at least in part on a historical clinical outcome database, and the one or more pruned action-state combinations are determined based at least in part on one or more pruned clinical actions that are selected from a plurality of candidate clinical actions based at least in part on one or more action pruning criteria. Improving accuracy of the noted predictive outputs in turn: (i) decreases the number of computational operations performed by processing units of predictive data analysis systems, thus increasing the computational efficiency of predictive data analysis systems, (ii) decreases the overall likelihood of system failure given a constant per-recommendation likelihood failure, thus increasing operational reliability of predictive data analysis systems, and (iii) increases the overall number of end-users that the predictive data analysis system can serve given a constant per-user query count, thus increasing the operational throughput of predictive data analysis systems. Accordingly, various embodiments of the present disclosure make important technical contributions to the field of predictive data analysis by improving computational efficiency, operational reliability, and operational throughput of predictive data analysis systems.

VI. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
   training a dynamics machine learning model based at least in part on one or more state transitions from a historical outcome database;
   identifying, by one or more processors, one or more data features from the historical outcome database;
   generating, by the one or more processors, a current state based at least in part on the one or more data features;
   identifying, by the one or more processors, a plurality of candidate actions for the current state from the historical outcome database;
   identifying, by the one or more processors, one or more pruned action-state combinations based at least in part on the current state, the plurality of candidate actions for the current state, and one or more action pruning criteria;
   generating, by the one or more processors and using the dynamics machine learning model, a plurality of next-state predictions for the one or more pruned action-state combinations;
   generating, by the one or more processors and using a state action handler, one or more familiarity-adjusted reward measures for the one or more pruned action-state combinations, wherein at least one of the familiarity-adjusted reward measures for a pruned action-state combination is based at least in part on an occurrence rate of the pruned action-state combination within a training dataset for the dynamics machine learning model; and
   identifying, by the one or more processors and using an agent machine learning model, an optimal action for the current state based at least in part on an inferred reinforcement learning policy that is determined based at least in part on the one or more familiarity-adjusted reward measures.

2. The computer-implemented method of claim 1, wherein each of the one or more action pruning criteria is determined based at least in part on at least one of suboptimal action patterns across the historical outcome database, underutilized action patterns across the historical outcome database, or non-recommended action patterns described by one or more clinical guideline data objects.

3. The computer-implemented method of claim 1, further comprising generating, using a reward generation machine learning model, a familiarity-adjusted reward function based at least in part on the one or more familiarity-adjusted reward measures.

4. The computer-implemented method of claim 3, further comprising:
   extracting, using a state encoder machine learning model, one or more defined clinical states based at least in part on the historical outcome database; and
   generating, using the state encoder machine learning model, a clinical state encoding.

5. The computer-implemented method of claim 4 further comprising generating, using the dynamics machine learning model, a next-state prediction for a particular action-state combination based at least in part on the clinical state encoding for a defined clinical state that is associated with the particular action-state combination from the one or more defined clinical states.

6. The computer-implemented method of claim 3, further comprises determining a clinical intervention recommendation that comprises a plurality of proposed optimal clinical interventions comprising diagnostic and surgical procedures, pharmaceuticals, and lifestyle/behavioral changes beginning with an optimal clinical intervention.

7. The computer-implemented method of claim 6, wherein determining the clinical intervention recommendation comprises;
identifying a modified clinical intervention based at least in part on one or more provider modifications to the optimal clinical intervention, where the modified clinical intervention is determined based at least in part on optimality criteria selected based at least in part on patient preferences as indicated based at least in part on one or more recorded communications between a patient and a physician; and
determining, based at least in part on the familiarity-adjusted reward function and using the agent machine learning model, an updated clinical intervention recommendation that comprises a plurality of modified optimal clinical interventions beginning with the modified clinical intervention.

8. The computer-implemented method of claim 6, wherein;
each proposed optimal clinical intervention in the plurality of proposed optimal clinical interventions is associated with a predefined clinical recommendation score; and
in response to determining that the predefined clinical recommendation score for a particular proposed optimal clinical intervention satisfies a first threshold but fails to satisfy a second threshold, one or more manual review operations are performed with respect to the particular proposed optimal clinical intervention.

9. A computing system comprising memory and one or more processors communicatively coupled to the memory, the one or more processors configured to:
train a dynamics machine learning model based at least in part on one or more state transitions from a historical outcome database;
identify one or more data features from the historical outcome database;
generate a current state based at least in part on the one or more data features;
identify a plurality of candidate actions for the current state from the historical outcome database;
identify one or more pruned action-state combinations based at least in part on the current state, the plurality of candidate actions for the current state, and one or more action pruning criteria;
generate, using the dynamics machine learning model, a plurality of next-state predictions for the one or more pruned action-state combinations;
generate, using a state action handler, one or more familiarity-adjusted reward measures for the one or more pruned action-state combinations, wherein at least one of the familiarity-adjusted reward measures for a pruned action-state combination is based at least in part on an occurrence rate of the pruned action-state combination within a training dataset for the dynamics machine learning model; and identify using an agent machine learning model, an optimal action for the current state based at least in part on an inferred reinforcement learning policy that is determined based at least in part on the one or more familiarity-adjusted reward measures.

10. The computing system of claim 9, wherein each of the one or more action pruning criteria is determined based at least in part on at least one of suboptimal action patterns across the historical outcome database, underutilized action patterns across the historical outcome database, or non-recommended action patterns described by one or more clinical guideline data objects.

11. The computing system of claim 9, wherein the one or more processors are configured to generate, using a reward generation machine learning model, a familiarity-adjusted reward function based at least in part on the one or more familiarity-adjusted reward measures.

12. The computing system of claim 11, wherein the one or more processors are configured to:
extract, using a state encoder machine learning model, one or more defined clinical states based at least in part on the historical outcome database; and
generate, using the state encoder machine learning model, a clinical state encoding.

13. The computing system of claim 12, wherein the one or more processors are configured to generate, using the dynamics machine learning model, a next-state prediction for a particular action-state combination based at least in part on the clinical state encoding for a defined clinical state that is associated with the particular action-state combination from the one or more defined clinical states.

14. The computing system of claim 11, wherein the one or more processors are further configured to determine a clinical intervention recommendation that comprises a plurality of proposed optimal clinical interventions comprising diagnostic and surgical procedures, pharmaceuticals, and lifestyle/behavioral changes beginning with an optimal clinical intervention.

15. The computing system of claim 14, wherein one or more processors are configured to determine the clinical intervention recommendation by:
identifying a modified clinical intervention based at least in part on one or more provider modifications to the optimal clinical intervention, where the modified clinical intervention is determined based at least in part on optimality criteria selected based at least in part on patient preferences as indicated based at least in part on one or more recorded communications between a patient and a physician; and
determining, based at least in part on the familiarity-adjusted reward function and using the agent machine learning model, an updated clinical intervention recommendation that comprises a plurality of modified optimal clinical interventions beginning with the modified clinical intervention.

16. The computing system of claim 14, wherein:
each proposed optimal clinical intervention in the plurality of proposed optimal clinical interventions is associated with a predefined clinical recommendation score; and
in response to determining that the predefined clinical recommendation score for a particular proposed optimal clinical intervention satisfies a first threshold but fails to satisfy a second threshold, the one or more processors are configured to perform one or more manual review operations with respect to the particular proposed optimal clinical intervention.

17. One or more non-transitory computer-readable storage media including instructions that, when executed by one or more processors, cause the one or more processors to:
- train a dynamics machine learning model based at least in part on one or more state transitions from a historical outcome database;
- identify one or more data features from the historical outcome database;
- generate a current state based at least in part on the one or more data features;
- identify a plurality of candidate actions for the current state from the historical outcome database;
- identify one or more pruned action-state combinations based at least in part on the current state, the plurality of candidate actions for the current state, and one or more action pruning criteria;
- generate, using the dynamics machine learning model, a plurality of next-state predictions for the one or more pruned action-state combinations;
- generate, using a state action handler, one or more familiarity-adjusted reward measures for the one or more pruned action-state combinations, wherein at least one of the familiarity-adjusted reward measures for a pruned action-state combination is based at least in part on an occurrence rate of the pruned action-state combination within a training dataset for the dynamics machine learning model;
- determine one or more pruned action-state combinations based at least in part on one or more pruned clinical actions that are selected from a plurality of candidate clinical actions based at least in part on one or more action pruning criteria;
- generate, using a reward generation machine learning model, a familiarity-adjusted reward function based at least in part on the plurality of next-state predictions for the one or more pruned action-state combinations based at least in part on the historical outcome database; and
- identify using an agent machine learning model, an optimal action for the current state based at least in part on an inferred reinforcement learning policy that is determined based at least in part on the one or more familiarity-adjusted reward measures.

18. The one or more non-transitory computer-readable storage media of claim 17, wherein each of the one or more action pruning criteria is determined based at least in part on at least one of suboptimal action patterns across the historical outcome database, underutilized action patterns across the historical outcome database, or non-recommended action patterns described by one or more clinical guideline data objects.

19. The one or more non-transitory computer-readable storage media of claim 17 further including instructions that, when executed by one or more processors, cause the one or more processors to generate, using a reward generation machine learning model, a familiarity-adjusted reward function based at least in part on the one or more familiarity-adjusted reward measures.

20. The one or more non-transitory computer-readable storage media of claim 19 further including instructions that, when executed by one or more processors, cause the one or more processors to:
- extract, using a state encoder machine learning model one or more defined clinical states based at least in part on the historical outcome database; and
- generate, using the state encoder machine learning model, a clinical state encoding.

* * * * *

UNITED STATES PATENT AND TRADEMARK OFFICE
CERTIFICATE OF CORRECTION

PATENT NO. : 12,062,449 B2
APPLICATION NO. : 17/538521
DATED : August 13, 2024
INVENTOR(S) : Reem A. Hussain et al.

Page 1 of 1

It is certified that error appears in the above-identified patent and that said Letters Patent is hereby corrected as shown below:

In the Claims

In Column 27, Line 13, Claim 7, delete "comprises;" and insert -- comprises: --, therefor.

In Column 27, Line 30, Claim 8, delete "wherein;" and insert -- wherein: --, therefor.

In Column 28, Line 39, Claim 15, delete "wherein" and insert -- wherein the --, therefor.

Signed and Sealed this
Twenty-ninth Day of October, 2024

Katherine Kelly Vidal
*Director of the United States Patent and Trademark Office*